United States Patent
Simaan et al.

(10) Patent No.: US 10,406,026 B2
(45) Date of Patent: Sep. 10, 2019

(54) SYSTEM AND METHOD FOR MACRO-MICRO DISTAL DEXTERITY ENHANCEMENT IN MICRO-SURGERY OF THE EYE

(75) Inventors: Nabil Simaan, New York, NY (US); Russell H. Taylor, Baltimore, MD (US); James T. Handa, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1376 days.

(21) Appl. No.: 12/992,519

(22) PCT Filed: May 18, 2009

(86) PCT No.: PCT/US2009/044388
§ 371 (c)(1),
(2), (4) Date: Feb. 8, 2011

(87) PCT Pub. No.: WO2009/140688
PCT Pub. Date: Nov. 19, 2009

(65) Prior Publication Data
US 2011/0125165 A1    May 26, 2011

Related U.S. Application Data

(60) Provisional application No. 61/127,860, filed on May 16, 2008.

(51) Int. Cl.
*A61F 9/00* (2006.01)
*A61B 34/00* (2016.01)
(Continued)

(52) U.S. Cl.
CPC ............ *A61F 9/007* (2013.01); *A61B 34/30* (2016.02); *A61B 34/35* (2016.02); *A61B 34/72* (2016.02);
(Continued)

(58) Field of Classification Search
CPC ............ A61F 9/007; A61B 2019/2203; A61B 2019/2211; A61B 2019/2249; A61B 34/30; A61B 2034/301; A61B 34/72
See application file for complete search history.

(56) References Cited

U.S. PATENT DOCUMENTS 5,318,528 A * 6/1994 Heaven .................. A61B 17/29
                                                600/564
5,410,638 A * 4/1995 Colgate et al. ............... 700/264
(Continued)

FOREIGN PATENT DOCUMENTS

WO    WO-2001-049183        7/2001
WO    WO-2001-049352 A2    7/2001
(Continued)

OTHER PUBLICATIONS

R. Taylor et al., "A Telerobotics Assistant for Laproscopic Surgery," in IEEE Engineering in Medicine and Biology Magazine, vol. 14, 1995, pp. 279-288.
(Continued)

*Primary Examiner* — Katrina M Stransky
*Assistant Examiner* — Lindsey Bachman
(74) *Attorney, Agent, or Firm* — Venable LLP; Henry J. Daley

(57) ABSTRACT

A system for operating within an interior region of the eye, or other organ, includes a delivery channel having a proximal portion located exterior to the eye and a distal portion positionable within the interior region of the eye, wherein the distal portion of the delivery channel defines an outer diameter that is smaller than or equal to about 18 gauge, and a micro-robot extendable from the distal portion of the delivery channel, wherein the micro-robot is remotely operable to change shape within the interior region of the eye.

21 Claims, 6 Drawing Sheets

(51) Int. Cl.
*A61B 34/30* (2016.01)
*A61B 34/35* (2016.01)
*A61F 9/007* (2006.01)

(52) U.S. Cl.
CPC ....... *A61B 2034/305* (2016.02); *A61F 9/0017* (2013.01); *Y10T 29/49826* (2015.01)

(56) References Cited

U.S. PATENT DOCUMENTS

| | | | |
|---|---|---|---|
| 5,649,956 | A | 7/1997 | Jensen et al. |
| 6,436,107 | B1 | 8/2002 | Wang et al. |
| 6,659,939 | B2 | 12/2003 | Moll et al. |
| 6,843,793 | B2 | 1/2005 | Brock et al. |
| 6,858,005 | B2 | 2/2005 | Ohline et al. |
| 6,999,852 | B2 | 2/2006 | Green |
| 2003/0120305 | A1* | 6/2003 | Jud et al. .................. 606/205 |
| 2005/0059960 | A1 | 3/2005 | Simaan et al. |
| 2006/0047302 | A1* | 3/2006 | Ortiz ............... A61B 17/07207 606/205 |
| 2006/0250664 | A1* | 11/2006 | Chien ............... H04N 1/028 358/474 |
| 2007/0055291 | A1* | 3/2007 | Birkmeyer ......... A61B 19/201 606/130 |
| 2007/0173975 | A1* | 7/2007 | Schena ................. A61B 19/22 700/245 |
| 2008/0188800 | A1* | 8/2008 | Bencini ............. A61M 25/0136 604/95.01 |
| 2008/0202274 | A1* | 8/2008 | Stuart ................. A61B 19/22 74/490.02 |
| 2008/0255544 | A1* | 10/2008 | Gielen ............... A61B 17/3403 606/1 |
| 2009/0012533 | A1* | 1/2009 | Barbagli ............. G06F 19/3406 606/130 |
| 2009/0048610 | A1* | 2/2009 | Tolkowsky .......... A61B 19/201 606/130 |

FOREIGN PATENT DOCUMENTS

| | | |
|---|---|---|
| WO | WO-2001-068016 A2 | 9/2001 |
| WO | WO-3006-207845 | 11/2005 |
| WO | WO-2008/036304 A2 | 3/2008 |

OTHER PUBLICATIONS

Kumar, R. et al."Preliminary Experiments in Cooperative Human/Robot Force Control for Robot Assisted Microsurgical Manipulation ," Int. Conf. on Robotics and Automation, San Francisco, CA, USA, pp. 1-8.

Simaan, N. et al., "High Dexterity Snake-like Robotic Slaves for Minimally Invasive Telesurgery of the Upper Airway," MICCAI, LNCS 3217, 2004, pp. 17-24.

Simaan, N. et al., "A Dexterous System for Laryngeal Surgery: Multi-Backbone Bending Snake-like Slaves for Teleoperated Dextrous Surgical Tool Manipulation," IEEE International Conference on Robotics and Automation, pp. 351-357, 2004.

International Search Report and Written Opinion for PCT/US2009/044388.

Ikuta et al., "Micro Active Forceps with Optical Fiber Scope for Intra-Occular Microsurgery," Department of Opthamology Shiga University of Medical Science, 1996 IEEE, pp. 456-461.

* cited by examiner

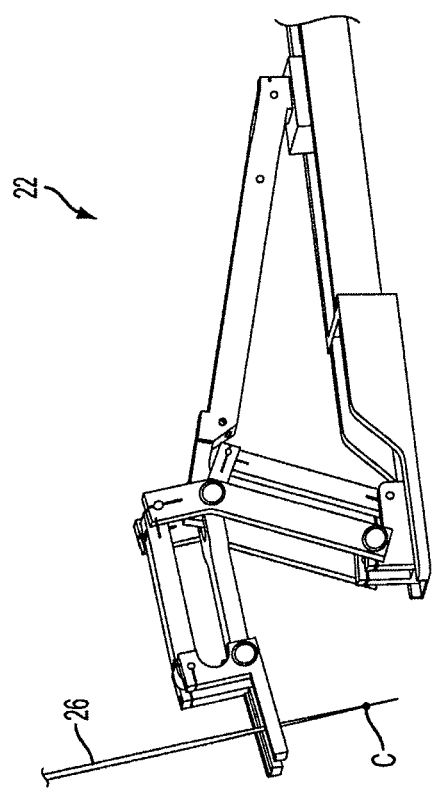
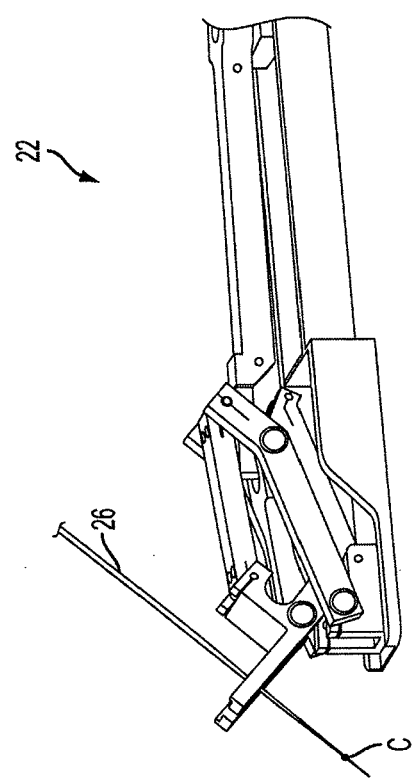

SYSTEM AND METHOD FOR MACRO-MICRO DISTAL DEXTERITY ENHANCEMENT IN MICRO-SURGERY OF THE EYE

CROSS-REFERENCE TO RELATED APPLICATIONS

This patent application claims the priority benefit under 35 U.S.C. § 119(e)(1) of U.S. Provisional Application No. 61/127,860, filed on May 16, 2008, the entire content of which is incorporated herein by reference, and is a U.S. national stage application under 35 U.S.C. § 371 of PCT/US2009/044388 filed May 18, 2009, the entire contents of which are incorporated herein by reference. All of the references cited in U.S. Provisional Application No. 61/127,860 are expressly incorporated herein by reference.

STATEMENT REGARDING FEDERALLY SPONSORED RESEARCH OR DEVELOPMENT

This application was made with Government support, under Grant Nos. EEC-9731748 and IIS-9801684 awarded by the National Science Foundation (NSF). The Government has certain rights in the invention.

TECHNICAL FIELD

This patent application relates generally to robotic-assisted surgery. More specifically, this patent application relates to an apparatus for robotic-assisted micro-surgery of the eye, and related methods.

BACKGROUND

Eye micro-surgery typically requires surgeons to perform high accuracy operations targeting micro blood vessels with characteristic dimensions ranging from about 10-400 µm in diameter. These operations may involve, for example, retinal peeling, separation of crossing blood vessels (sheethothamy), blood vessel cannulation, and drug delivery.

Minimally invasive surgery of the eye is typically constrained to four degrees-of-freedom (DoF) motion through a fixed fulcrum point in the sclera. For example, surgeons are currently limited to using straight rigid needles that have no dexterity at their tip. This lack of dexterity can be a drawback in many types of eye surgery, such as those mentioned above.

Due to the dimensions of the blood vessels and veins involved in eye micro surgery, surgeons are required to operate with high accuracy while maintaining a fixed point of entry through the sclera. Thus, accuracy and tremor reduction are currently major limiting factors in eye micro-surgery.

Lack of force feedback is another limiting factor in eye micro-surgery. For example, the amount of force required to poke through the retina is very small (on the order of one milli-newton). Therefore, in manual operations, surgeons have to maintain a training schedule to maintain their ability, for example, to deliver drugs to the retina without poking through the choroids.

In view of the foregoing, there exists a need in the art for a system and method for macro-micro distal dexterity enhancement in micro-surgery of the eye.

SUMMARY

Further aspects, objectives, and advantages, as well as the structure and function of exemplary embodiments, will become apparent from a consideration of the description, drawings, and examples.

According to an illustrative embodiment, a system for operating within an interior region of an eye comprises a delivery channel having a proximal portion located exterior to the eye and a distal portion positionable within the interior region of the eye, wherein the distal portion of the delivery channel defines an outer diameter that is smaller than or equal to about 18 gauge, and a micro-robot extendable from the distal portion of the delivery channel, wherein the micro-robot is remotely operable to change shape within the interior region of the eye.

According to another illustrative embodiment, a system for operating within an interior region of an eye comprises a bending delivery channel having a proximal portion located exterior to the eye and a distal portion positionable within the interior region of the eye, the distal portion defining an outer diameter that is smaller than or equal to about 18 gauge, wherein the distal portion of the bending delivery channel is remotely operable to bend within the interior region of the eye.

According to another illustrative embodiment, a method of manufacturing a surgical system comprises providing a delivery channel having a proximal portion and a distal portion, wherein the distal portion defines an outer diameter that is smaller than or equal to about 18 gauge, and providing a micro-robot positioned to extend from the distal portion of the delivery channel.

BRIEF DESCRIPTION OF THE DRAWINGS

The foregoing aspects and other features and advantages of the invention will be apparent from the following drawings, wherein like reference numbers generally indicate identical, functionally similar, and/or structurally similar elements.

FIGS. 2A and 2B are perspective views of an illustrative remote center of motion mechanism of the system of FIG. 1, shown in a first position and a second position, respectively;

DETAILED DESCRIPTION

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without departing from the spirit and scope of the invention. All references cited herein are incorporated by reference as if each had been individually incorporated.

Figure 1:
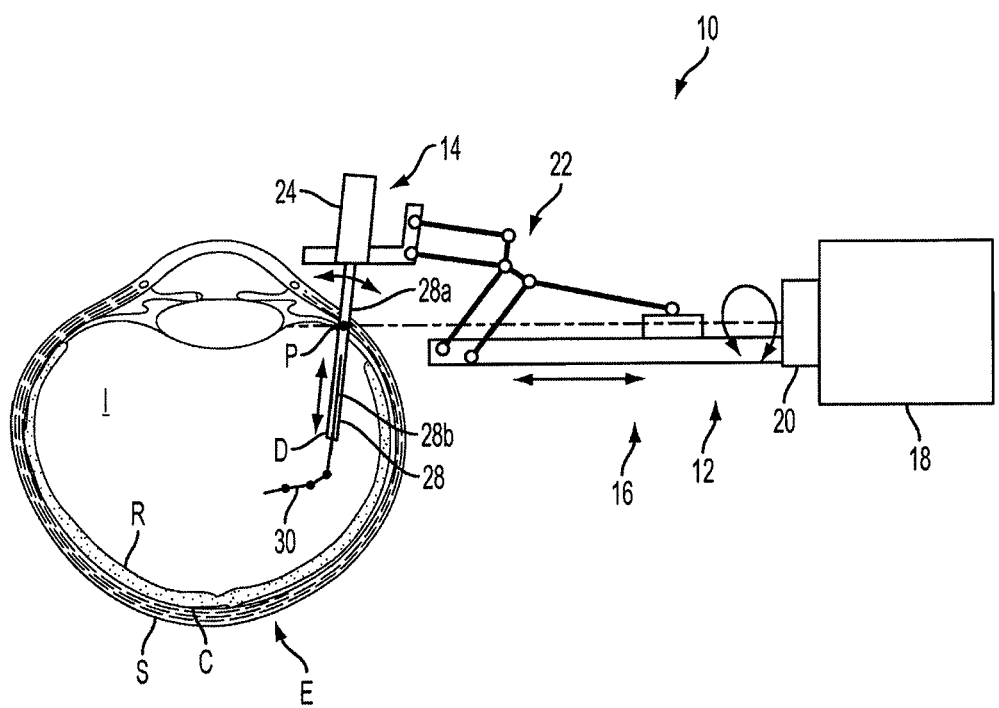
FIG. 1 is side view of a robotic-assisted surgical system according to a first illustrative embodiment of the present invention.

Referring to FIG. 1, a first illustrative embodiment of a robotic-assisted surgical system according to the present invention is shown. The system 10 may be used, for example, in micro-surgery of organs, for example, hollow organs, such as the human eye, however, other applications are possible. For sake of convenience, the system 10 will be described herein primarily in the context of micro-surgery of the human eye.

Still referring to FIG. 1, the system 10 may comprise a remote positioning unit 12 located exterior to the eye E, and a macro-micro distal dexterity (MMDD) robot 14 supported by the remote positioning unit 12. As shown in FIG. 1, a portion of the MMDD robot 14 may extend into the interior portion I of the eye E, as will be described in more detail hereinafter.

Generally, the remote positioning unit 12 may comprise any unit that is located exterior to the eye E, and supports the MMDD with respect to the eye E. According to an illustrative embodiment, the remote positioning unit 12 may comprise a remote center of motion (RCM) unit 16. As shown, the RCM unit 16 can allow the surgeon to manipulate the MMDD robot 14 in four degree-of-freedom (DoF) motion while keeping the fulcrum point (e.g., fixed insertion point P) through which the MMDD robot 14 protrudes into the interior portion I of the eye E fixed in space, thereby minimizing the size of the fixed insertion point P into the eye E.

Still referring to FIG. 1, the RCM unit 16 may comprise, for example, a seven DoF robot composed from a three DoF Cartesian robot, such as an x-y-z stage 18, a rotation stage 20, an RCM mechanism 22, and a two DoF z-theta stage 24. The x-y-z stage 18, rotation stage 20, and RCM mechanism 22 can together provide a two DoF tilt motion around the fixed insertion point P. The z-theta stage 24 can provide both axial motion and rotation about the axis of a tool passing through the fixed insertion point P. In an illustrative embodiment, the Cartesian robot 18 may only be used for global positioning of the fixed insertion point P on the eye E, however, other uses of the Cartesian robot 18 are contemplated. The RCM unit 16 may be used, for example, as a tele-operated slave robot while the surgeon looks through a microscope, or it can be used in cooperative manipulation. According to an alternative embodiment, the x-y-z stage 18 can be replaced with a passive fixture mechanism (not shown).

Referring to FIGS. 2A and 2B, an illustrative embodiment of the RCM mechanism 22 is shown in more detail. As shown, the RCM mechanism 22 can comprise an optimized planar six bar mechanism that is dimensioned to maintain a fixed remote center of motion C of a tool supported by the RCM mechanism 22, for example, a portion of the MMDD robot 14 (not shown in FIGS. 2A and 2B). In practice, the fixed center of motion C can be located at the same point as the fixed insertion point P on the eye. Further details regarding an illustrative RCM unit 16 for use with the present invention are described in R. Taylor et al., "A Telerobotics Assistant for Laproscopic Surgery," in IEEE Engineering in Medicine and Biology Magazine, vol. 14, 1995, pp. 279-288, the entire content of which is incorporated herein by reference. The RCM unit 16 can be tele-actuated by the surgeon, or it can be used as a cooperative manipulation robot, such as the Steady Hand robot presented in R. Kumar et al., "Preliminary Experiments in Cooperative Human/Robot Force Control for Robot Assisted Microsurgical Manipulation," Int. Conf. on Robotics and Automation, San Francisco, Calif., USA, pp. 610-616, 2000, the entire content of which is incorporated herein by reference.

Referring back to FIG. 1, the MMDD robot 14 may provide the surgeon with dexterity inside the eye. As shown, an illustrative embodiment of the MMDD robot 14 can comprise a macro distal dexterity unit, shown for example as a delivery channel 28, and a micro distal dexterity unit, shown for example as a micro-robot 30. The delivery channel 28 can have a proximal portion 28a located exterior to the eye E and coupled to the remote positioning unit 12, and a distal portion 28b that is located within the interior portion I of the eye E. According to the illustrative embodiment shown in FIG. 1, the delivery channel 28 can be rigid and non-bendable, however, in other illustrative embodiments described hereinafter, the delivery channel can be bendable.

As shown in FIG. 1, at least the distal portion 28b of the delivery channel 28 can define an outer diameter D. According to an illustrative embodiment, the outer diameter D can be equal to or smaller than about 18 gauge (about 1.270 mm). As used herein, the term "gauge" refers to the outer diameter, for example, of the delivery channel, as defined by the Stubs Iron Wire Gauge system. An outer of diameter D of 18 gauge or smaller can be important for eye surgery, where the insertion point P needs to be as small as possible. According to an illustrative embodiment, the outer diameter D can be between about 20 gauge (about 0.902 mm) and about 25 gauge (about 0.508 mm). With an outer diameter D between about 20 gauge and about 25 gauge, it is generally possible to operate on the eye E without having to use sutures to close the insertion point P after the procedure.

The macro distal dexterity unit can provide the surgeon with the ability to remotely control the position of the distal tip of delivery channel 28 in the interior region I of the eye E, while the micro distal dexterity unit can provide true distal dexterity of the micro-robot 30. According to an illustrative embodiment, the surgeon can command the position and orientation of the micro-robot 30 through a telemanipulation control architecture, for example, that has a local position/velocity controller on the master side, a local position/velocity controller on the slave side, and a telemanipulation high level controller. This can be a standard telemanipulation architecture in which the master provides impedance feedback to the surgeon.

Lower level control of the macro distal dexterity unit and the micro distal dexterity unit can rely on the commands of the high-level telemanipulation controller, for example, using standard redundancy resolution algorithms, such as, for example, pseudo-inverse methods, augmented Jacobian methods, extended Jacobian methods, and task screw decomposition methods for redundancy resolution.

The micro distal dexterity unit, e.g., micro-robot 30 may be used to perform micro-surgical procedures, for example, on blood vessels of the choroid layer C of the eye E (i.e., located between the sclera S and the retina R), however, other applications are possible. The micro distal dexterity unit, e.g., micro-robot 30, can be delivered to its location of interest inside the eye E by the macro distal dexterity unit, e.g., delivery channel 28. Several illustrative embodiments of the macro distal dexterity unit and micro distal dexterity unit are described below.

Still referring to FIG. 1, an illustrative embodiment of the present invention is shown where the macro distal dexterity unit comprises a rigid delivery channel 28, and the micro distal dexterity unit comprises a micro-robot 30 in the form of an elongated, bendable, finger-like device. According to the illustrative embodiment shown, the proximal portion 28a of the delivery channel 28 can be supported by the RCM unit 16, such that the surgeon can control the RCM unit 16 to position the distal portion 28b of the rigid delivery channel 28 within the interior region I of the eye E through the fixed insertion point P. The elongated, bendable micro-robot 30 can be delivered through the rigid delivery channel 28.

As used herein, the term micro-robot generally refers to any device (e.g., an electro-mechanical device), such as a robot or tele-robot, that can be delivered into the interior region I of the eye E or other small volume organ through a delivery channel according to the present invention, and is remotely operable by a surgeon to change shape (e.g., bend, pivot, rotate) or otherwise maneuver within the interior region I of the eye E, or other small volume organ. According to an illustrative embodiment, the micro-robot can be characterized by dimensions on the order of about 1-2 mm or less (in contrast to, e.g., a "small" robot characterized by dimensions on the order of about 10 cm). The surgeon can remotely operate the micro-robot 30 to change shape, e.g., bend sideways, within the interior region I of the eye E, for example, to manipulate a micro knife located at the tip of the micro-robot 30. The micro knife can be used, for example, to perform micro-surgical procedures on blood vessels of the choroid layer C of the eye E. According to an illustrative embodiment, electro-active polymers (EAP), Micro-Electro-Mechanical Systems (MEMS), and/or piezoelectric elements can be used to change the shape of the micro-robot 30 within the interior region I of the eye E, however, other configurations are possible. Further details about micro-robot 30 are described below.

According to an illustrative embodiment, the micro-robot 30 can be controlled using a proportional-integral-derivative (PID) controller to control voltage provided to EAP actuators in the micro-robot 30. For example, the EAP actuators may be pre-calibrated for bending at a specific angle as a function of their control voltage, and the control can be implemented on the low level by controlling the applied voltage.

Figure 3:
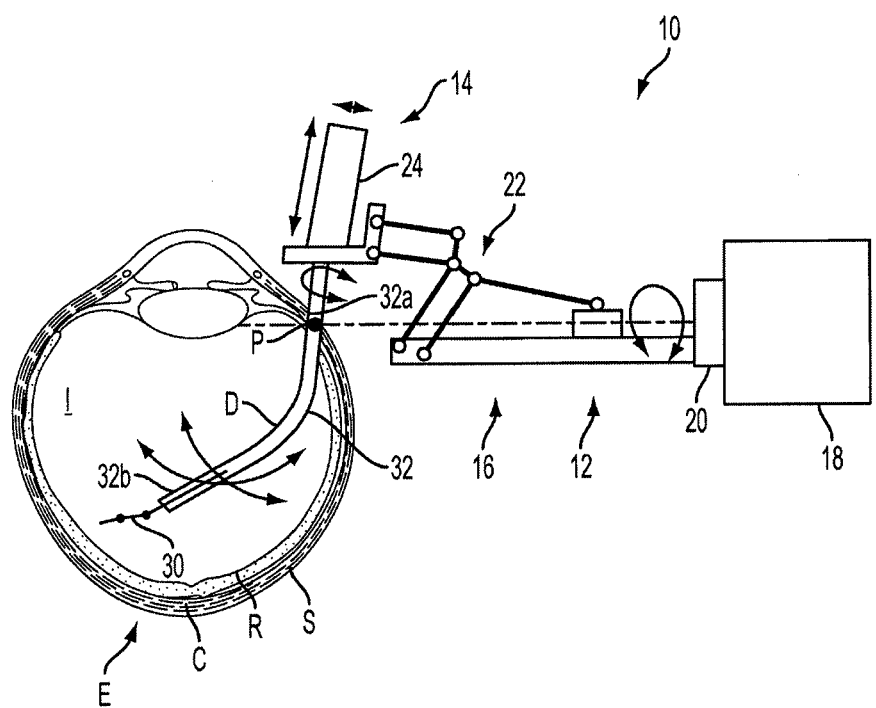
FIG. 3 is a side view of a robotic-assisted surgical system according to a second illustrative embodiment of the present invention.

Referring to FIG. 3, another illustrative embodiment of the present invention is shown, which is similar to that of FIG. 1, except the rigid delivery channel 28 of FIG. 1 is replaced by an active bending delivery channel 32. A surgeon can remotely control at least the distal portion 32b of the bending delivery channel 32 to bend within the interior region I of the eye E, for example, to provide dexterity inside the eye and/or to orient the tip of the delivery channel 32 in proximity to the region of interest within the eye E (e.g., under the retina R). According to an illustrative embodiment, the bending delivery channel may be made from a precurved NiTi tube that bends in a predetermined shape as it is extended out of a straight cannula, using, for example, PID position control. However, further details regarding another illustrative embodiment of the active bending delivery channel 32 are provided below in connection with FIG. 5. In the illustrative embodiment of FIG. 3, the x-y-z stage 18 can be replaced with a passive fixture mechanism (not shown).

Still referring to FIG. 3, at least the distal portion 32b of the delivery channel 32 can define an outer diameter D. According to an illustrative embodiment, the outer diameter D can be equal to or smaller than about 18 gauge (about 1.270 mm). According to another illustrative embodiment, the outer diameter D can be between about 20 gauge (about 0.902 mm) and about 25 gauge (about 0.508 mm).

Figure 4:
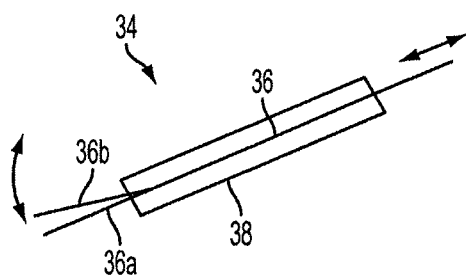
FIG. 4 is a side view of a mechanical tweezers according to an illustrative embodiment of the present invention.

Referring to FIG. 4, an illustrative embodiment of a mechanical tweezers according to the present invention is shown. According to an illustrative embodiment, the mechanical tweezers 34 may be used in place of the micro-robot 30 of FIGS. 1 and 3. The mechanical tweezers 34 can comprise, for example, a pre-shaped element 36 that is slidable within a micro-tube 38, or within the delivery channel. The pre-shaped element 36 can comprise, for example, first and second jaws 36a, 36b that are pre-bent into the open position (shown). The pre-shaped element can be constructed from a super-elastic material, such as NiTi. When the micro-tube 38 is pressed forward toward the distal end of the pre-shaped element 36, engagement between the micro-tube 38 and the jaws 36a, 36b can press the jaws 36a, 36b towards one another (e.g., closed). This may facilitate grasping a blood vessel or other structure within the eye E. Moving the jaws 36a, 36b within the micro-tube 38 can also facilitate insertion and/or removal of the mechanical tweezers 34 from the eye E through the fixed insertion point P. According to another illustrative embodiment (not shown), a hook, needle holder, or other device can be constructed using similar principles to the mechanical tweezers 34.

According to another illustrative embodiment, the micro-robot 30 of FIG. 3 can be replaced with a pseudo dexterity device (not shown) extending from the distal portion 32b of the bending delivery channel 32. According to an illustrative embodiment, the pseudo dexterity device may comprise a super-elastic link that has been previously pre-set into a circular arc or other shape. When this link is extended from inside the distal portion 32b of the delivery channel 32, the link may bend into its pre-set shape, for example, sideways in different arcs. Various embodiments of the pseudo dexterity device may include, without limitation, a super-elastic micro-needle used for cannulation and drug delivery, a super-elastic wire equipped with mechanical tweezers (e.g., similar to FIG. 4), and/or a super-elastic micro-tube carrying within it a fiber-optic line (e.g., attached to an external laser light source for localized laser treatment of micro blood vessels), although other configurations are possible. In illustrative embodiments, such pseudo dexterity devices are characterized by dimensions on the order of about 1-2 mm.

Figure 5:
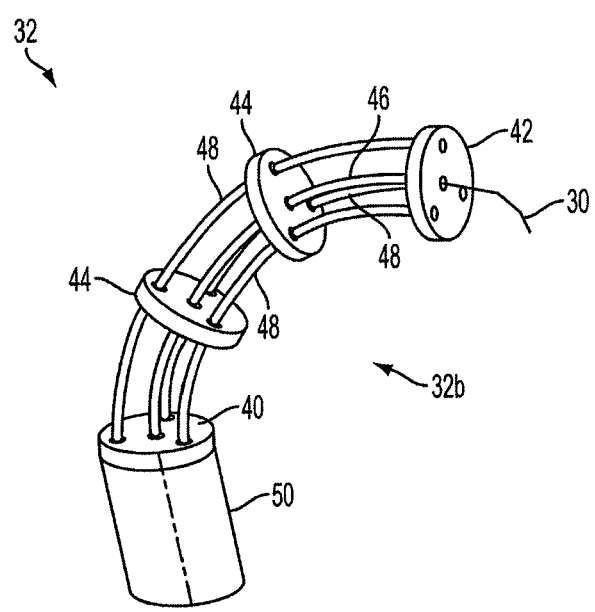
FIG. 5 is a perspective view of an illustrative bending delivery channel of the system of FIG. 3.

Referring to FIG. 5, an illustrative embodiment of the active bending delivery channel 32 is shown. The bending delivery channel 32 may be remotely operated by a surgeon to gain dexterity inside the eye E, for example, by bending the distal portion 32b of the delivery channel 32. According to an illustrative embodiment, the bending delivery channel 32 may comprise a two DoF robot including a base disk 40, an end disk 42, and a plurality of spacer disks 44 located between the base disk 40 and end disk 42. The bending delivery channel 32 may also comprise a primary or central backbone 46 and a plurality of secondary backbones 48 distributed around the central backbone 46. According to an illustrative embodiment, the backbones 46, 48 may comprise super-elastic tubes, for example, made from NiTi, although other configurations and materials are possible. According to an illustrative embodiment, there may be three secondary backbones 48 arranged equidistant from the central backbone 46 and from one another, as shown, although other configurations are possible.

Still referring to FIG. 5, according to an illustrative embodiment, the central backbone 46 may be fixed to both the base disk 40, the end disk 42, and all of the spacer disks 44, while the secondary backbones 48 may be fixed to only the end disk 42. Accordingly, the secondary backbones 48 may be free to slide and bend through properly dimensioned holes 50 in the base disk 40 and the spacer disks 44. As a result, the secondary backbones 48 may be remotely actuated by the surgeon in both push and pull modes to bend the bending delivery channel 32.

For example, the bending delivery channel 32 may be the backbone of a continuum robot, wherein the bending delivery channel 32 can be bent in any direction by controlling (e.g., pushing/pulling) the length of one or more of the secondary backbones 48. For example, PID position control can be utilized on actuators that control the lengths of the secondary backbones 48. Further details regarding control of the bending delivery channel 32 can be found in Simaan, N. et al., "High Dexterity Snake-like Robotic Slaves for Minimally Invasive Telesurgery of the Upper Airway," MICCAI 2004—the 7th International Conference on Medical Image Computing and Computer-Assisted Intervention, Saint Malo, France, Sep. 26-30, 2004, and in Simaan, N. et al., "A Dexterous System for Laryngeal Surgery: Multi-Backbone Bending Snake-like Slaves for Teleoperated Dextrous Surgical Tool Manipulation," IEEE International Conference on Robotics and Automation, pp. 351-357, 2004. The entire content of the foregoing two publications is incorporated herein by reference.

According to an illustrative embodiment, the spacer disks 44 can prevent buckling of the central backbone 46 and/or the secondary backbones 48, and/or can maintain an equal distance between them. As shown in FIG. 5, the base disk 40 may be mounted on a tubular snake holder 50, for example, which forms part of the delivery channel 32. The microrobot 30, mechanical tweezers (not shown), pseudo dexterity device (not shown), or other tool may extend from the central backbone 46, although other configurations are possible. According to an illustrative embodiment, the base disk 40, end disk 42, and spacer disks 44 can define an outer diameter of the bending delivery channel 32 that is smaller than, or equal to about 18 gauge (about 1.270 mm). According to another illustrative embodiment, these components can define an outer diameter between about 20 gauge (about 0.902 mm) and about 25 gauge (about 0.508 mm). According to an illustrative embodiment, the bending delivery channel 32 can define a length of about 9 mm between the base disk 40 and the end disk 42.

The illustrative embodiment of FIG. 5 can provide one or more advantages over conventional designs using discrete backbones (e.g., articulated serial chains). For example, by using flexible backbones 46, 48, the dependency on small joints and wires may be removed, which in turn may reduce manufacturing costs and/or enhance downsize scalability. The use of tubes for the backbones 46, 48 can also provide secondary applications. For example, the backbones 46, 48 can be used to pass wires or other structures used to actuate tool(s) mounted on the end disk 42. Alternatively, the tubular backbones can be used to pass light, for example, to provide a light source of light for imaging.

By using three push-pull secondary backbones for actuation, it may be possible to satisfy the statics of the structure while preventing buckling of the backbones 46, 48. This can further enhance the downsize scalability while maintaining the force application capability of the bending delivery channel 32. Further details regarding a bending delivery channel suitable for use with the present invention can be found in U.S. Patent Application Publication No. 2005/0059960 A1, published Mar. 17, 2005, the entire content of which is incorporated herein by reference.

According to an illustrative embodiment, the central backbone 46 can have several applications. For example, the central backbone 46 can act as a delivery channel for a flexible straight cannulation needle, a micro-robot, or a pseudo-dexterity device, such as a pre-set shape memory alloy (SMA) bent needle used for cannulation. Additionally or alternatively, the central backbone 46 can act as a light source by carrying within it an optical fiber. Additionally or alternatively, the central backbone 46 can act as a bending needle for drug delivery.

According to an illustrative embodiment, one or more of the secondary backbones 48 can be used for carrying a fiber-optic light source inside them. This can provide the surgeons with an internal controllable light source. According to an alternative embodiment (shown in FIG. 6), one or more of the secondary backbones 48 can comprise simple super-elastic NiTi wires instead of tubes, for example, to enhance downsize scalability, but in this case the possibility of using the secondary backbones for guiding a fiber optic light source may be lost.

According to an illustrative embodiment, the secondary backbones 48 can be constructed to be very flexible in bending but stiff in the axial direction. According to this illustrative embodiment, the secondary backbones 48 can be supported in a flexible sheath to prevent buckling in a long flexible section. This embodiment may permit the system to be used in flexible endoscopy applications and/or in intracavitary procedures, such as, e.g., ablations inside the heart.

In order to obtain true micro-distal dexterity for microvascular surgery, it may be advantageous to provide a controllable micro-robot at the end of the delivery channel 28, 32. For example, according to an illustrative embodiment, the micro-robot can have multiple joints for performing cannulation of blood vessels and/or separation of crossing blood vessels. According to an illustrative embodiment, the micro-robot can utilize EAPs, such as, for example, conjugated conductive polymers (CP), for actuation of the micro-robot.

Figure 6:
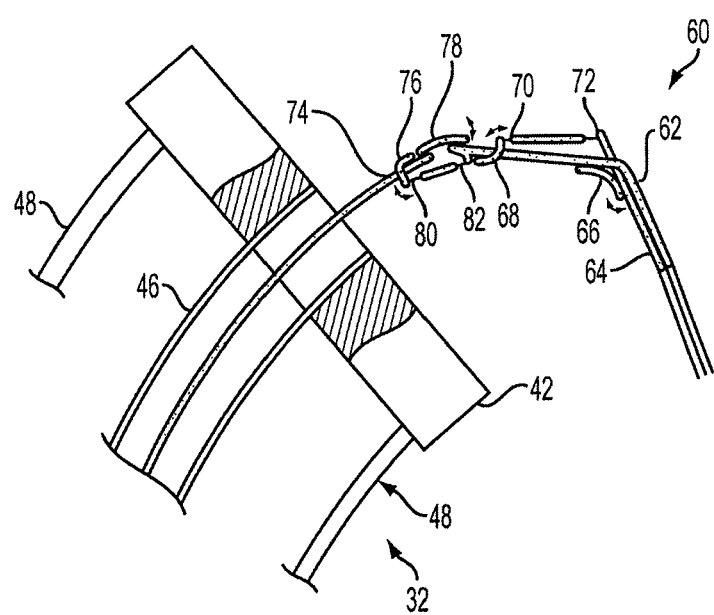
FIG. 6 is a schematic representation of an illustrative bending delivery channel supporting a micro-robot including a gripper according to an illustrative embodiment of the present invention.

Referring to FIG. 6, an illustrative embodiment of a micro-robot 60 according to the present invention is shown. The micro-robot 60 is shown extending from the distal portion of a bending delivery channel 32, which is similar to that shown in FIG. 5, except in FIG. 6 the delivery channel 32 has solid secondary backbones 48 instead of tubular ones. However, according to an alternative embodiment, the micro-robot 60 can be delivered through a rigid or other type of delivery channel.

As shown in FIG. 6, the micro-robot 60 can comprise a gripper including a first jaw 62 and a second jaw 64 which can move with respect to one another between a closed position (shown) and an open position (not shown), for example, using counteracting conjugated polymer joints 66, 68 and flexures 70, 72. As also shown in FIG. 6, the micro-robot 60 can be mounted at the end of a wire 74 extending through the central backbone 46, and can pivot or bend with respect to the wire 66, for example, using counteracting conjugated polymer joints 76, 78 and flexures 80, 82. The conjugated polymer joints 66, 68, 76, 78 can comprise, for example, bi-morph electro-active joints, each being made of a fixed length thin sheet of conductive material covered on each side by a layer of electro active polymer.

As mentioned previously, illustrative embodiments can utilize EAPs as actuators for moving, bending, or otherwise operating the micro-robot 30. According to an illustrative embodiment, the sub-class of EAPs called ionic polymers (IP) may be used, since they feature low actuation voltages, biocompatibility, operation in bodily fluids, and high payload-to-weight ratio. According to another illustrative embodiment, IPs such as ionomeric polymer metal composites (IPMC) (e.g., Nafion® based actuators), and conjugated polymers (e.g., PPy based actuators) may be used. For example, an IPMC micro-scale single cell manipulation finger may be used for the micro-robot. According to an illustrative embodiment, such a micro-robot can be fabricated, for example, using MEMS technology. According to another illustrative embodiment, the conjugated polymers can be used to form the micro-robot as a two DoF robot equipped with a 3-fingered gripper for single cell manipulation.

The aforementioned systems and methods can be used in various medical applications in the eye, such as, for example, separation of crossed veins (sheethothamy), cannulation of occluded blood vessels, drug delivery, and/or providing an active bending light source. Additionally or alternatively, they can be used to transmit a laser light source, for example, for laser eye treatment. Additionally or alternatively, they can be used for other cannulation procedures, injections, or microsurgical manipulations in neurosurgery, spine surgery, or general minimally invasive surgery. Additionally or alternatively, they can be used for micromanipulation of ablation devices in the heart and elsewhere, minimally-invasive evacuation or treatment of osteolytic lesions inside bones, minimally-invasive evacuation of hematomas, and/or localized biopsy. These applications are illustrative and not exhaustive. Other applications will be readily apparent to those skilled in the surgical arts.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. For example, the active bending delivery channel does not necessarily have to be mounted to an RCM robot. It could alternatively be mounted, for example, on the distal end of a flexible device such as a catheter or flexible endoscope. Further, systems can be constructed both with and without a micro-robot located at the end of the delivery channel. Similarly, systems can be constructed with the micro-robot at the end of a rigid delivery channel, or at the end of a flexible delivery channel other than what is disclosed herein. It is therefore to be understood that, within the scope of the claims and their equivalents, the invention may be practiced otherwise than as specifically described.

The invention claimed is:

1. A system for operating within an interior region of an eye, comprising:
a bendable delivery channel having a proximal portion configured to be located exterior to the eye and a distal portion configured to be positionable within the interior region of the eye, wherein the distal portion of the bendable delivery channel has an outer diameter that is smaller than or equal to about 18 gauge;
an electro-mechanical device extendable from within the distal portion of the bendable delivery channel; and
a telemanipulation control system comprising a controller and is in communication with the electro-mechanical device and the bendable delivery channel,
wherein the electro-mechanical device is configured to be remotely operable to articulate and change shape within the interior region of the eye in response to the telemanipulation control system, and
wherein the telemanipulation control system is configured to be located exterior to the eye and comprises a remote center of motion unit configured to use commands from the controller to manipulate the bendable delivery channel in at least four degrees of freedom with respect to a fixed fulcrum point, and the electro-mechanical device in at least two degrees of freedom with respect to the bendable delivery channel, within the interior region of the eye.

2. The system of claim 1, wherein the electro-mechanical device comprises an elongated finger extending from the distal portion of the bendable delivery channel, and the elongated finger is remotely operable to bend within the interior region of the eye.

3. The system of claim 2, further comprising a knife coupled to the elongated finger.

4. The system of claim 1, wherein the electro-mechanical device comprises an electro-active polymer.

5. The system of claim 4, wherein the electro-active polymer comprises at least one of a conjugated conductive polymer, an ionic polymer, and an ionomeric polymer metal composite.

6. The system of claim 1, wherein the electro-mechanical device comprises a gripper extendable from the distal portion of the bendable delivery channel.

7. The system of claim 1, wherein the distal portion is remotely operable to bend within the interior region of the eye.

8. The system of claim 1, wherein the remote center of motion unit comprises a planar six bar mechanism supporting a z-theta stage coupled to the bendable delivery channel.

9. The system of claim 1, wherein the electro-mechanical device comprises:
a first jaw;
a second jaw movable with respect to the first jaw between an open position and a closed position;
a first CP joint positioned to move the second jaw to the open position; and
a second CP joint positioned to move the second jaw to the closed position.

10. The system of claim 1, wherein the distal portion of the bendable delivery channel defines an outer diameter that is between about 20 gauge and about 25 gauge.

11. The system of claim 1, wherein said change of shape of said electro-mechanical device comprises at least one of a change of position and a change of orientation of the electro-mechanical device.

12. The system of claim 1, wherein said telemanipulation control system controls a position of said distal portion within said interior region of said eye.

13. The system of claim 1, wherein said electro-mechanical device comprises at least one of an electro-active polymer, a micro-electro-mechanical system, and a piezoelectric element.

14. The system of claim 1, wherein said telemanipulation control system uses standard redundancy resolution algorithms.

15. The system of claim 1, wherein the bendable delivery channel is made up of an NiTi tube.

16. A system for operating within an interior region of an eye, comprising:
a macro-micro robot comprising a bendable delivery channel and an electro-mechanical device, the bendable delivery channel having a proximal portion configured to be located exterior to the eye and a distal portion configured to be positionable within the interior region of the eye, the distal portion of the bendable delivery channel having an outer diameter that is smaller than or equal to about 18 gauge, and the electro-mechanical device comprising an elongated finger extendable from within the distal portion of the bendable delivery channel; and a telemanipulation control system in communication with the electro-mechanical device and the bendable delivery channel of the macro-micro robot, wherein the elongated finger is configured to be remotely operable to articulate and change shape within the interior region of the eye in response to the telemanipulation control system, wherein the telemanipulation control system includes at least a remote center of motion unit configured to be located exterior to the eye and allow manipulation of the electro-mechanical device within the interior region of the eye, and wherein the telemanipulation control system is configured to be located exterior to the eye and comprises a remote center of motion unit configured to manipulate the bendable delivery channel in at least four degrees of freedom with respect to a fixed fulcrum point, and the electro-mechanical device in at least two degrees of freedom with respect to the bendable delivery channel, within the interior region of the eye.

17. The system of claim 16, wherein the remote center of motion unit is capable of permitting manipulation of the macro-micro robot in four degrees of freedom while keeping a fixed insertion point through which the bendable delivery channel protrudes within the interior region of the eye.

18. The system of claim 17, wherein the remote center of motion unit comprises a cartesian robot and a remote positioning unit, the cartesian robot capable of positioning the fixed insertion point on the eye, and the remote positioning unit capable of supporting the macro-micro robot.

19. The system of claim 18, wherein the remote positioning unit comprises a planar six bar mechanism configured to maintain a fixed center of motion of a portion of the macro-micro-robot.

20. The system of 18, wherein the remote center of motion unit further comprises a rotation stage capable of rotating the remote positioning unit.

21. The system of claim 20, wherein the cartesian robot, the remote positioning unit, and the rotation stage are capable of together providing two degrees of freedom around the fixed center of motion of the portion of the macro-micro-robot.

* * * * *